United States Patent [19]

Hylton et al.

[11] 4,072,698

[45] Feb. 7, 1978

[54] RESOLUTION OF AMINONITRILES

[75] Inventors: Thomas A. Hylton, Kalamazoo; Francis L. Shenton, Portage, both of Mich.

[73] Assignee: The Upjohn Company, Kalamazoo, Mich.

[21] Appl. No.: 746,932

[22] Filed: Dec. 2, 1976

[51] Int. Cl.² ............... C07C 121/78; C07C 121/80
[52] U.S. Cl. .................. 260/465 E; 260/326.14 R; 260/326.15; 260/329 AM; 260/332.2 A; 260/340.3; 260/340.5 R; 260/347.3; 260/347.7; 260/464; 260/465.5 R; 260/519; 260/557 R; 260/558 A; 260/561 A
[58] Field of Search ............ 260/465 E, 464, 465.5 R, 260/340.5 R, 347.7, 329 AM, 326.15

[56] References Cited

U.S. PATENT DOCUMENTS

| | | | |
|---|---|---|---|
| 3,366,679 | 1/1968 | Reinhold et al. | 260/519 |
| 3,480,670 | 11/1969 | Reinhold et al. | 260/465 E X |
| 3,808,254 | 4/1974 | Matthews | 260/465 E X |
| 3,890,379 | 6/1975 | Schawartz | 260/519 |
| 3,976,680 | 8/1976 | Clark et al. | 260/471 A |

*Primary Examiner*—Dolph H. Torrence
*Attorney, Agent, or Firm*—Bruce Stein; Roman Saliwanchik

[57] ABSTRACT

The present invention is a chemical method for obtaining an optically pure 2-aminonitrile or a 2-aminoamide from (1) an optically impure mixture, (2) a racemic mixture, or (3) the optically pure enantiomer of the opposite configuration, in an amount greater than actually present, by use of optically active acids with a ketone or an aldehyde catalyst. Yields of greater than 70 percent of one enantiomer are obtained from racemic mixtures in very short time periods.

37 Claims, No Drawings

RESOLUTION OF AMINONITRILES

BACKGROUND OF THE INVENTION

2-Aminonitriles of the formula:

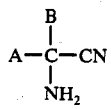

or 2-aminoamides of the formula:

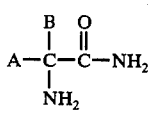

where A is not equal to B contain an asymmetric center at the C-2 or alpha (a) carbon atom. The presence of an asymmetric center results in two molecules, which are enantiomers, or mirror images of each other. Each enantiomer is optically active: one rotates plane polarized light to the right and is termed dextrorotatory ($d$ or +) and the other enantiomer rotates plane polarized light to the left and is termed levorotatory (1 or −). Rotation of plane polarized light by enantiomers is to an equal degree but in opposite directions. The enantiomers by convention are designated D and L (relative configuration) and/or S and R (absolute configuration). See E. L. Eliel, Stereochemistry of Carbon Compounds. McGraw-Hill, 1962, p. 88. When an equal number of $d$ and 1 enantiomeric molecules exist together, a racemic (optically inactive) mixture results. When an unequal number of $d$ and 1 enantiomeric molecules exist together an optically impure mixture results.

Formulas I and II above as well as formulas III and V below do not designate a particular stereochemical configuration. Therefore, they may represent an enantiomer, its mirror image, a racemic form, or an optically impure form, in which the enantiomers are not present in equal numbers.

It is well known that when a biologically active compound contains a center of a symmetry which produces two enantiomers, one of the enantiomers often possesses most or all of the biological activity. In such cases the other enantiomer is biologically inactive, and is therefore an impurity. Examples are sugars (D-glucose), amino acids (phenylglycine and phenylalanine), LSD, and the prostaglandins. Therefore, it is highly advantageous from a pharmaceutical point of view to obtain the biologically active enantiomer in an optically pure form from an optically impure or racemic mixture.

The hydrolysis of 2-aminonitriles to the corresponding 2-aminoacids (a-aminoacids) is well known. The hydrolysis of amides such as those of formula II to the corresponding acid is also well known to those skilled in the art. Since the hydrolysis does not involve reaction at the asymmetric center no change in relative or absolute configuration takes place during the hydrolysis reaction. Therefore, if one starts with an optically active 2-aminonitrile one obtains the corresponding optically active 2-aminoacid. Likewise, if one starts with a racemic 2-aminonitrile one obtains a racemic 2-aminoacid. See for example Gr. Brit. Pat. No. 1,382,688; Basic Principles of Organic Chemistry, J. D. Roberts and M. C. Caserio, W. A. Benjamin, Inc., N. Y., 1964, page 706; Advanced Organic Chemistry Reactions Mechanisms and Structure, J. March, McGraw-Hill, 1968, p. 660; U.S. Pat. No. 3,890,379 and J. Schawartz et al., Chem. Ind. 1698 (1968).

The biological activity of the 2-aminoacids usually resides with only one of the enantiomers. The optically active 2-aminoacids are commercially important for the production of various antibiotics, in particular cephalosporins and penicillins as is well known to those skilled in the art. The optically active 2-aminoacids are also useful in resolution of optically impure compounds as is also well known to those skilled in the art. Since the 2-aminoacids are usually obtained by hydrolysis of the corresponding 2-aminonitrile or 2-aminoamide it would be highly desirable to be able to obtain the desired 2-aminonitrile or 2-aminoamide in optically pure form prior to the hydrolysis reaction.

Methods of resolving racemic mixtures into their optically pure enantiomers are well known to those skilled in the art. See for example, Roberts and Caserio, supra, page 497; March, supra, page 92, and Eliel, supra, pages 47-85. Perhaps the most general resolution procedure is to form diastereomers from the enantiomers. In the case of 2-aminonitriles or 2-aminoamides this is best done by salt formation with an optically active acid and then recovery of one of the diastereomers by fractional crystallization. The recovered diastereomer is then neutralized to obtain the optically pure enantiomer.

With regard to 2-aminonitriles, H. Reihlen, E. Weinbrenner, and G. v Hessling, Ann. 534,247 (1938) reported the resolution (low yield) of racemic 2-aminophenylacetonitrile using optically active tartaric acid.

Since a racemic mixture contains equal numbers of the D and L enantiomers, resolution of a racemic mixture provides 50% of the total amount of the compound present in optically pure form, i.e., one of the enantiomers. Until 1974 a 50% yield of an optically pure enantiomer from a racemic mixture of 2-aminonitriles was considered optimal. U.S. Pat. No. 3,941,796 discloses a one-step method for resolution with racemization of α-amino-ε-caprolactams so as to obtain yields of greater than 50% of the desired enantiomer. The process utilizes a strong base, a metal ion, a derivative of a chelating carbonyl compound and seed crystals. The present invention not only does not require a strong base, a metal ion or seed crystals but does not require that the carbonyl compound (aldehyde or ketone) be a chelating agent.

U.S. Pat. No. 3,808,254 discloses the use of alkanoic acids to improve the resolution of α-aminophenylacetonitrile using optically active tartaric acid. This is the first published report which describes obtaining yields greater than 50% of one enantiomer from a racemic mixture. U.S. Pat. No. 3,808,254 further discloses a reaction time for resolution of 2-aminophenylacetonitrile ". . . ranging from about 4 hours to about 72 hours, preferably about 8 to about 15 hours." The actual times disclosed by examples 1 thru 9 of U.S. Pat. No. 3,808,254 are "overnight", "one day", "a day", and "several days". The method of the present invention for obtaining optically pure 2-aminonitriles and 2-aminoamides does not use alkanoic acids and has the surprising and unexpected result of obtaining optically pure 2-aminoarylacetonitriles in amounts greater than originally present in 1 hour or less. From a commercial point of view this is a distinct advantage over prior processes.

Gr. Brit. Pat. No. 1,423,822 dicloses a process for resolution of amino acid esters by use of optically active tartaric acid and an aldehyde or ketone. The process of Great Britain Pat. No. 1,423,822 differs from the process of the present invention in that the process of Great Britain Pat. No. 1,423,822 is a process for resolving a racemic mixture of α-aminoacid esters whereas the present process is a process for producing optically pure 2-aminonitriles and 2-aminoamides. Both processes use optically active acids and aldehydes or ketones. The present invention has a surprising and unexpected result of having much shorter reaction times. For example, even though Great Britain Pat. No. 1,423,822 states that reaction times of 20-24 hours is usual and can be as low as 6-8 hours, the examples set forth in Great Britain Pat. No. 1,423,822 disclose much longer times. For instance, in Example 1 the solution was stirred for 5 days. In Table A the reaction times for use of aldehydes in the resolution process are from 18-70 hours. Using ketones for the resolution process the reaction times are 44-288 hours, see Table B.

BRIEF DESCRIPTION OF THE INVENTION

The definitions and explanations below are for the terms as used throughout the entire patent application including both the specification and the claims.

All temperatures are in degrees Centigrade.

SSB refers to Skellysolve B ® a mixture of isomeric hexanes.

THF refers to tetrahydrofuran.

DMF refers to dimethylformamide.

DMAC refers to dimethylacetamide.

$[\alpha]_D^{25}$ ($c = 1$, water) refers to the angle of rotation of plane polarized light (specific optical rotation) at 25° with the sodium D line (5893A) with a concentration of 1 g./100 ml. in distilled water.

R is alkyl of 1 thru 6 carbon atoms; cycloalkyl of 3 thru 6 carbon atoms; aromatic of 6 thru 10 carbon atoms, substituted with 0 thru 3 substituents, which may be the same or different and are selected from the group consisting of alkyl of 1 thru 6 carbon atoms, hydroxyl, alkoxy where the alkyl group contains 1 thru 6 carbon atoms, cyclic alkylenedioxy where the alkylene group contains 1 thru 3 carbon atoms, halogen, trifluoromethyl, and cyano; aralkyl of 7 or 8 carbon atoms substituted with 0 thru 3 substituents, which may be the same or different and are selected from the group consisting of alkyl of 1 thru 6 carbon atoms, hydroxyl, alkoxy where the alkyl group contains 1 thru 6 carbon atoms, or cyclic alkylenedioxy where the alkylene group contains 1 thru 3 carbon atoms; 2- or 3-furyl; 2- or 3-thienyl; and 2- or 3-indolylmethyl.

$R_1COR_2$ (IV) is a compound where $R_1$ and $R_2$ may be the same or different, with the proviso that $R_1$ and $R_2$ cannot both be aromatic, and when $R_2$ is not hydrogen $R_1$ and $R_2$ taken together with the attached carbon atom may form a cyclic ketone selected from the group consisting of cyclobutanone, cyclopentanone, cyclohexanone, and cycloheptanone.

$R_1$ is alkyl of 1 thru 6 carbon atoms; cycloalkyl of 4 thru 6 carbon atoms; aromatic of 6 thru 10 carbon atoms, substituted with 0 thru 3 substituents selected from the group consisting of alkyl of 1 thru 6 carbon atoms, halogen, or alkoxy where the alkyl group contains 1 thru 6 carbon atoms; or aralkyl of 7 or 8 carbon atoms.

$R_2$ is hydrogen or $R_1$.

Disclosed is a process for producing an optically pure 2-aminonitrile enantiomer of the formula:

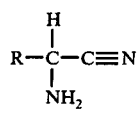

III in acid salt form in an amount greater than present in an optically impure 2-aminonitrile (III) mixture which comprises contacting the optically impure 2-aminonitrile (III) mixture with an optically active acid in the presence of a compound of the formula $R_1COR_2$ (IV), the methyl or ethyl acetal, ketal, hemi-acetal, or hemi-ketal thereof and separating the diastereomeric acid salt of the optically pure 2-aminonitrile (III) enantiomer. R, $R_1COR_2$ (IV), $R_1$ and $R_2$ are defined above.

Also disclosed is a process for resolving a racemic 2-aminonitrile mixture to greater than 50% yield of one enantiomer of the formula:

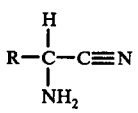

III in acid salt form which comprises contacting the racemic 2-aminonitrile (III) with an optically active acid in the presence of a compound of the formula $R_1COR_2$ (IV), the methyl or ethyl acetal, ketal, hemi-acetal, or hemi-ketal thereof and separating the diastereomeric acid salt of the optically pure 2-aminonitrile (III) enantiomer. R, $R_1COR_2$ (IV), $R_1$ and $R_2$ are defined above.

Also disclosed is a process for producing an optically pure 2-aminonitrile enantiomer of the formula:

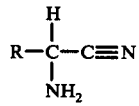

III in acid salt form which comprises contacting the optically pure 2-aminonitrile (III) enantiomer of the opposite configuration with an optically active acid in the presence of a compound of the formula $R_1COR_2$ (IV), the methyl or ethyl acetal, ketal, hemi-acetal or hemi-ketal thereof and separating the diastereomeric acid salt of the optically pure 2-aminonitrile (III) enantiomer. R, $R_1COR_2$ (IV), $R_1$ and $R_2$ are defined above.

Disclosed is a process for producing an optically pure 2-aminoamide enantiomer of the formula:

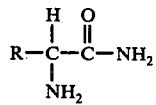

V in acid salt form, in an amount greater than present in an optically impure 2-aminoamide (V) mixture, which comprises contacting the optically impure 2-aminoamide (V) mixture with an optically active acid in the presence of a compound of the formula $R_1COR_2$ (IV), the methyl or ethyl acetal, ketal, hemi-acetal, or hemi-ketal thereof and separating the diastereomeric acid salt of the optically pure 2-aminoamide (V) enantiomer. R, $R_1COR_2$ (IV), $R_1$ and $R_2$ are defined above.

Further disclosed is a process for resolving a racemic 2-aminoamide mixture to greater than 50% yield of one enantiomer of the formula:

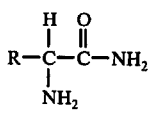   V in acid salt form which comprises contacting the racemic 2-aminoamide (V) with an optically active acid in the presence of a compound of the formula $R_1COR_2$ (IV), the methyl or ethyl acetal, ketal, hemi-acetal, or hemi-ketal thereof, and separating the diastereomeric acid salt of the optically pure 2-aminoamide (V) enantiomer. R, $R_1COR_2$ (IV), $R_1$ and $R_2$ are defined above.

Further disclosed is a process for producing an optically pure 2-aminoamide enantiomer of the formula:

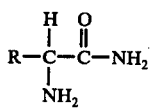   V in acid salt form which comprises contacting the optically pure 2-aminoamide (V) enantiomer of the opposite configuration with an optically active acid in the presence of a compound of the formula $R_1COR_2$ (IV), the methyl or ethyl acetal, ketal, hemi-acetal, or hemi-ketal thereof, and separating the diastereomeric acid salt of the optically pure 2-aminoamide (V) enantiomer. R, $R_1COR_2$ (IV), $R_1$ and $R_2$ are defined above.

DETAILED DESCRIPTION OF THE INVENTION

The process of the present invention for producing optically pure 2-aminonitrile or 2-aminoamide enantiomers of the formulas:

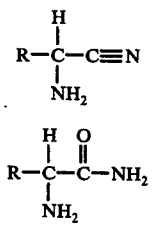

respectively in amounts greater than that originally present, comprises contacting an optically impure mixture, a racemic mixture, or an enantiomer of the opposite configuration (opposite optical rotation) with an optically active acid in the presence of a compound of the formula $R_1COR_2$ (IV), the methyl or ethyl acetal, ketal, hemi-acetal or hemi-ketal thereof and separating the diastereomeric acid salt of the optically pure 2-aminonitrile (III) or 2-aminoamide (V) enantiomer.

Both the 2-aminonitriles (III) and the 2-aminoamides (V) are primary amines.

The present invention is applicable to three different circumstances. One is in obtaining an optically pure 2-aminonitrile (III) or 2-aminoamide (V) enantiomer from an optically impure mixture where the desired 2-aminonitrile (III) or 2-aminoamide (V) enantiomer is present in a range of from about 5 to about 95%. By prior art methods it was possible to obtain the desired enantiomer from the optically impure mixture in an amount equal to that which was present. For example, if the desired enantiomer was present in 20% then the undesired enantiomer was present in 80%. Prior art methods permitted isolation of about 20 g. of the desired enantiomer from a 100 g. mixture. By use of the present invention in the above example it is possible to obtain substantially more than a 20 g. yield of the desired enantiomer.

A second and probably the most useful way of practicing the present invention is where the optically impure mixture is a racemic mixture. By prior art methods beginning with 100 g. of a racemic 2-aminonitrile (III), only 50 g. of the optically pure desired 2-aminonitrile (III) enantiomer could be isolated. By the present invention substantially more than 50 g. of the desired optically pure 2-aminonitrile (III) enantiomer can be obtained beginning with a racemic mixture.

A third method of practicing the present invention is to obtain a desired optically pure enantiomer from the optically pure enantiomer of the opposite configuration. Hence, if one has an optically pure 2-aminonitrile (III) or 2-aminoamide (V) of a configuration opposite that of which is desired, by prior art methods it was not possible to obtain any of the desired 2-aminonitrile (III) or 2-aminoamide (V) enantiomer. By the process of the present invention it is possible to obtain substantial amounts of the desired optically pure 2-aminonitrile (III) or 2-aminoamide (V) enantiomer from the optically pure 2-aminonitrile (III) or 2-aminoamide (V) enantiomer of the opposite optical configuration, respectively.

It is preferred that the optically impure amine (III or V) mixture be a racemic structure.

The 2-aminonitriles (III) and the 2-aminoamides (V) of the present invention are of the formulas:

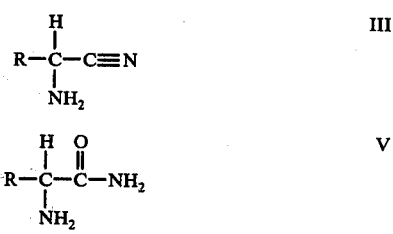

where R is defined above.

The 2-aminonitrile (III) and the 2-aminoamide (V) as diagramed are not meant to designate a particular stereochemical configuration such, as D or L, R or S, or $d$ or $l$. The particular enantiometer D or L, etc., that one wishes to produce by the present invention will vary and depend on what particular compound is desired, i.e., what the R group is in the amine (III or V). In some cases one will desire the D enantiomer and in other cases the L enantiomer. The process of the present invention is applicable to obtaining either enantiomer of a given compound provided that the reaction conditions are properly adjusted so that the desired amine (III or V) enantiomer in its diasteromeric salt form precipitates; these techniques are well known to those skilled in the art.

The particular 2-aminonitrile (III) or 2-aminoamide (V) enantiomer involved is defined by the R group. R is alkyl of one thru 6 carbon atoms. Examples of alkyl of one thru 6 carbon atoms include methyl, ethyl, propyl, butyl, pentyl, hexyl, and isomers thereof. R is cycloalkyl of 3 thru 6 carbon atoms. Examples of cycloalkyl of 3 thru 6 carbon atoms, include cyclopropyl, cyclobutyl, cyclopentyl and cyclohexyl. Examples of aromatic of 6 thru 10 carbon atoms substituted with 0 thru 3 substituents which may be the same or different and are selected from the group consisting of alkyl of one thru 6 carbon atoms, hydroxyl, alkoxy where the alkyl group contains one thru 6 carbon atoms, cyclic alkylenedioxy where the alkylene group contains one thru 3 carbon atoms, halogen, trifluoromethyl and cyano include phenyl, $\alpha$-naphthyl,$\beta$-naphthyl, p-methylphenyl, 2,4-dimethylphenyl, p-hydroxyphenyl, p-methoxyphenyl, o-chlorophenyl, 3-chloro-4-hydroxyphenyl, 3,4,5-trimethoxyphenyl, p-trifluoromethylphenyl, and 3-cyanophenyl. Examples of halogen include fluorine, chlorine, bromine, and iodine. Examples of aralkyl of 7 or 8 carbon atoms substituted with 0 thru 3 substituents, which may be the same or different and are selected from the group consisting of alkyl of 1 thru 6 carbon atoms, hydroxyl, alkoxy where the alkyl group contains 1 thru 6 carbon atoms or cyclic alkylenedioxy where the alkylene group contains 1 thru 3 carbon atoms include benzyl, 2-phenylethyl and 4-hydroxy-3-methoxybenzyl. It is preferred that R be aromatic as defined above. It is even more preferred that R be selected from the group consisting of phenyl, p-methoxyphenyl, p-hydroxyphenyl, 3-chloro-4-hydroxyphenyl, 2- or 3-furyl, or 2- or 3-thienyl. It is even more preferred that R be selected from the group consisting of phenyl, p-methoxyphenyl, and p-hydroxyphenyl. It is most preferred that R be phenyl.

The substitution of the R and the amino ($-NH_2$) groups on the alkyl chain of nitriles and amides may be designated by arabic numerals (1, 2, etc.) or Greek letters ($\alpha$, $\beta$, etc.). When using arabic numerals the carbon of the nitrile group and the carbon of the carbonyl is designated as carbon 1 and each carbon away from the nitrile or carbonyl group as an increasing number. When using the Greek letters, alpha ($\alpha$) is located at the carbon atom next to the nitrile or carbonyl group. Hence, $\alpha$-aminonitrile is the same as 2-aminonitrile.

Both the 2-aminonitriles (III) and the 2-aminoamides (V) are primary amines. These amines can and do form Schiff bases with aldehydes and ketones. Therefore, whenever the term 2-aminonitrile (III) or 2-aminoamide (V) is used in the practice of this invention it also means and does include not only the 2-aminonitrile (III) or 2-aminoamide (V) defined by it but also the Schiff bases produced from it where these derivatives are possible.

Various optically active acids may be used in the practice of this invention. Generally weak carboxylic acids such as tartaric acid are preferred. Suitable optically active carboxylic acid resolving agents include tartaric acid, diacetyl tartaric acid, dibenzoyl tartaric acid, di-p-toluyl tartaric acid, atrolactic acid, camphoric acid, 4-chlorotartranilic acid, hydratropic acid, malic acid, mandelic acid, menthoxyacetic acid, diisopropylidene-2-oxo-L-gulonic acid, and pyrrolidine-5-carboxylic acid. See S. H. Wilen, Tables of Resolving Agents and Optical Resolutions, Univ. of Notre Dame Press, Notre Dame, 1972, p. 224–229. See also E. L. Eliel, Stereochemistry of Carbon Compounds, McGraw-Hill Book Co., 1962, p. 52–57. It is preferred that the optically active acid be selected from the group consisting of tartaric acid, diacetyl tartaric acid, dibenzoyl tartaric acid, di-p-toluyl tartaric acid, malic acid, camphoric acid, menthoxyacetic or mandelic acid. It is more preferred that the optically active acid be tartaric acid. With the 2-aminonitriles (III) it is most preferred that the optically active acid be L-(+)-tartaric acid. Besides the optically active acids exemplified above other optically active carboxylic acids of similar acidity (pKa) can be used in the practice of the present invention. As one skilled in the art is not able to predict which enantiomeric 2-aminonitrile (III) or 2-aminoamide (V) will form the less soluble diastereomeric salt, this would have to be determined by simple experimentation as is well known to those skilled in the art. Likewise the solvent(s) will have to be properly chosen to effectuate the precipitation of the diastereomeric salt of the desired 2-aminonitrile (III) or 2-aminoamide (V) as is also well known to those skilled in the art.

The optically active acid used in producing the optically pure 2-aminonitrile (III) or 2-aminoamide (V) enantiomer in the present invention may be used in less than equimolar quantities as compared to the amine (III or V). A slight molar excess of the optically active acid may be used if desired.

The reaction of the present invention is catalyzed by a compound of the formula $R_1COR_2$ (IV), the methyl or ethyl acetal, ketal, hemi-acetal or hemi-ketal thereof where $R_1$ and $R_2$ may be the same or different with the proviso that both $R_1$ and $R_2$ cannot both be aromatic and when $R_2$ is not hydrogen $R_1$ and $R_2$ taken together with the attached carbon atom may form a cyclic ketone selected from a group consisting of cyclobutanone, cyclopentanone, cyclohexanone and cycloheptanone. $R_1$ and $R_2$ are defined above. Examples of alkyl, cycloalkyl, aromatic and aralkyl as defined for $R_1COR_2$ (IV) are the same as for R in compounds III and V. When $R_2$ is hydrogen, $R_1COR_2$ (IV) is $R_1CHO$ which is an aldehyde. When $R_2$ is not hydrogen, $R_1COR_2$ (IV) is a ketone. Aldehydes and ketones form acetals, ketals, hemi-acetals, and hemi-ketals with alcohols, as is well known to those skilled in the art. Since these aldehyde and ketone derivatives function as aldehydes and ketones, under the conditions of the practice of this invention whenever the term catalyst or $R_1COR_2$ (IV) is used it means and includes not only the aldehydes and ketones defined by it but also the corresponding methyl and ethyl acetals, ketals, hemi-acetals and hemi-ketals where these derivatives are possible.

It is preferred that the compound $R_1COR_2$ (IV) be a ketone or an aldehyde. It is more preferred that the compound $R_1COR_2$ (IV) be a ketone or aldehyde selected from the group consisting of acetone, 2-butanone and cyclohexanone. It is most preferred that the compound $R_1COR_2$ (IV) be acetone.

The amount of the $R_1COR_2$ catalyst (IV) is not critical. It is preferred that the amount of the catalyst present in the reaction mixture be one molar equivalent. However, lesser amounts are also effective to catalyze the reaction. Amounts of the catalyst greater than one molar equivalent may be used.

The catalyst may be added to the reaction mixture in various ways. The catalyst may be mixed with a diluent which contains the optically active acid. Alternatively, the catalyst may be added to the amine (III or V) in its liquid diluent. Also, the catalyst may be added to the mixture of the amine (III or V) and the optically active acid.

Suitable diluents for the optically active acid include aromatic hydrocarbon solvents (such as benzene, toluene, and xylene), short chain alcohols of 1 thru 6 carbon atoms, (such as methanol, ethanol, propanol, isopropanol and butanol), short chain ketones (such as acetone and 2-butanone), or cyclic ketones (such as cyclohexanone), esters (such as ethyl acetate), halogenated hydrocarbons (such as chloroform, methylene chloride, and carbon tetrachloride), ethers (such as diethyl ether, THF, and dioxane) and amides (such as DMF and DMAC). Aliphatic hydrocarbon solvents such as hexane or SSB are also suitable.

The 2-aminonitrile (III) or 2-aminoamide (V) in a liquid diluent is added to the optically active acid.

Diluents suitable for the 2-aminonitrile (III) or the 2-aminoamide (V) are the same as those used for the optically active acid. It is preferred that the 2-aminonitrile (III) or 2-aminoamide (V) be in solution although this is not necessary.

In the practice of the present invention the 2-aminonitrile (III) or the 2-aminoamide (V) can be added to the optically active acid or the other way around. However, when the optically active acid is a dicarboxylic acid it is often preferable to add the amine (III or V) to the optically active acid. The choice of a diluent for the acid is usually not critical. It is preferred that the optically active acid and the amine (III or V) be in solution although this is not critical. The important thing is for the desired diastereomeric salt to precipitate and separate from the reaction mixture in such a manner that it may be recovered in pure form.

The reaction temperature is not critical. It depends on the solubility of the optically active acid, the amine (III or V) to be resolved and the optically pure amine (III or V) salt. A suitable range is from about 0 to about 100°. The temperature range is governed primarily by the solubility of the desired diastereomeric amine (III or V) salt in the solvent system utilized.

The reaction mixture of the amine (III or V), optically active acid and catalyst is stirred for a time period ranging from a few minutes to a few days depending on the nature of the R group. The usual time period for 2-aminoarylacetonitriles is 1 hour or less. This is most surprising and unexpected in view of the prior art processes which were discussed previously. The time periods for specific experiments are found in the examples which follow. The reaction can be monitored by collecting small samples of the precipitate and observing the optical rotation. The reaction is complete when the optical rotation remains constant.

The work up of the reaction mixture will depend on which diluents were selected for the reaction. Generally it is desirable to select diluents for the reaction so that the optically pure diastereomeric salt will precipitate as it forms. The temperature is also influential on the precipitation of the diastereomeric salt for the reaction mixture. Upon precipitation of the optically pure diastereomeric salt, the reaction mixture is filtered, the precipitate is washed and dried under vacuum at a temperature of about 40° to 100° as is well known to those skilled in the art.

The diastereomeric salt of the desired amine (III or V) enantiomer thus obtained may be neutralized to obtain the desired 2-aminonitrile (III) or 2-aminoamide (V) enantiomer in free base form as is well known to those skilled in the art.

Alternatively, the diastereomeric salt of the desired 2-aminonitrile (III) or 2-aminoamide (V) enantiomer obtained thru the process of the present invention can be readily hydrolyzed to the corresponding 2-aminoacid by methods well known to those skilled in the art. The hydrolysis of the 2-aminonitrile (III) takes place readily under acid conditions by use of acids such as hydrochloric, sulfuric, or p-toluenesulfonic. The use of mineral acids is preferred. Refluxing for approximately 1 to 4 hours at a temperature of from about 50° to 150° produces 2-aminoacids in good yield. See Great Britain Pat. No. 1,382,687, in particular examples 10 thru 12. See also Great Britain Pat. No. 1,382,688. Hydrolysis of the 2-aminoamides (V) is performed under acidic or basic conditions. While nitrous acid is a very good agent for hydrolyzing amides in general, it is unsatisfactory here because of the primary amino group.

It is well known to those skilled in the art that the term "optically pure" means essentially one enantiomer but may contain small or trace amounts of the other enantiomer.

The 2-aminonitriles and 2-aminoamides within the scope of formulas III and V of the present invention are either known to those skilled in the art or can readily be prepared by methods well known to those skilled in the art.

The aldehydes and ketones within the scope of formula IV are either known to those skilled in the art or can be readily prepared by methods well known to those skilled in the art.

EXAMPLES the invention may be more fully understood from the following examples.

EXAMPLE 1

Resolution of Racemic 2-Amino-2-phenylacetonitrile Without a Catalyst (Formula III: R is phenyl)

A solution of racemic 2-amino-2-phenylacetonitrile (U.S. Pat. No. 3,808,254; 6.0 g., 0.045 mole) in 20 ml. of methanol:benzene (15:85 v/v) is added to a solution of L-(+)-tartaric acid (6.6 g., 0.044 mole) in methanol (20 ml.) at 40°. Upon stirring for about 15 minutes a precipitate is formed. The mixture is kept at 40° for 1 hour and then cooled to 20°. This precipitate, the product, is washed with methanol (10 ml.), and dried overnight at 40° under reduced pressure (40mm). The product is a mixture of the diastereomers of D- and L-2-amino-2-phenylacetonitrilehydrogen-L-(+)-tartrate, 5.90 g. (47% yield), $[\alpha]_D^{25}$ +36° ($c$ = 1, water).

EXAMPLE 2

Resolution of Racemic 2-Amino-2-phenylacetonitrile Without a Catalyst (Formula III: R is phenyl)

A solution of racemic 2-amino-2-phenylacetonitrile (6.0 g., 0.045 mole) is added to a solution of L-(+)-tartaric acid (6.6 g., 0.044 mole) in glacial acetic acid (56 ml.). The mixture is stirred at 42° forming a precipitate. After 1 hour the mixture is cooled to 20°. This precipitate, the product, is collected by filtration, washed with benzene, and dried overnight at 40° under reduced pressure (40 mm). The product is a mixture of the diastereomers of D- and L-2-amino-2-phenylacetonitrile-hydrogen-L-(+)-tartrate, 9.86g. (77% yield), $[\alpha]_D^{25}$ +20° ($c$ = 1, water).

EXAMPLE 3

Resolution of Racemic 2-Amino-2-phenylacetonitrile With Acetone as Catalyst (Formula III: R is phenyl; Formula IV: $R_1$ and $R_2$ are methyl)

Following the procedure of Example 1, acetone (2.0 ml., 0.027 mole) is included in the reaction mixture. The yield of D-(+)-2-amino-2-phenylacetonitrile-hydrogen- L-(+)-tartrate is 9.02g. (72% yield), $[\alpha]_D^{25}$ +43° ($c$ = 1, water).

EXAMPLE 4

Resolution of Racemic 2-Amino-2-phenylacetonitrile With Acetone as a Catalyst (Formula III: R is phenyl; Formula IV: $R_1$ and $R_2$ are methyl)

Following the procedure of Example 3, but replacing the solvent benzene with methanol, D-(+)-2-amino-2-phenylacetonitrile-hydrogen-L-(+)-tartrate is obtained, 8.92 g. (63% yield), $[\alpha]_D^{25}$ +43° ($c$ = 1, water).

EXAMPLE 5

Resolution of Racemic 2-Amino-2-phenylacetonitrile With Acetone as a Catalyst (Formula III: R is phenyl; Formula IV: $R_1$ and $R_2$ are methyl)

Following the procedure of Example 4 the acetone catalyzed reaction is repeated but substituting ethanol in place of methanol as a solvent D-(+)-2-amino-2-phenylacetonitrile-hydrogen-L-(+)-tartrate is obtained, 12.0 g. (85% yield), $[60]_D^{25}$ +43° ($c$ = 1, water).

Following the general procedure of Examples 3–5 but making noncritical variations the following experiments were performed at 40°.

| EXAMPLE | Molar Equivalent of acetone | Time (hr.) | Yield % | $[\alpha]_D^{25}$ |
|---|---|---|---|---|
| 6 | 1.0 | 1 | 79 | 45° |
| 7 | 1.0 | 0.25 | 79 | 45° |
| 8 | 1.0 | 0.5 | 85 | 46° |
| 9 | 1.0 | 2 | 84 | 44° |
| 10 | 1.0 | 4 | 78 | 44° |
| 11 | 4.0 | 1 | 80 | 45° |
| 12 | 1.0 | 1 | 80 | 45° |
| 13 | 3.0 | 0.5 | 78 | 47° |
| 14 | 1.5 | 1 | 77 | 46° |
| 15 | 1.5 | 1 | 81 | 45° |
| 16 | 0.25 | 1 | 83 | 45° |
| 17 | 1.0 | 1 | 76 | 46° |
| 18 | 1.0 | 1 | 88 | 46° |

In Examples 17 and 18 the solvent was methanol-:ethyl acetate, 3:7 v/v (Example 17) and 1:1 v/v (Example 18).

EXAMPLE 19

Resolution of Racemic 2-Amino-2-phenylacetonitrile With Benzaldehyde as the Catalyst (Formula III: R is phenyl; Formula IV: $R_1$ is phenyl and $R_2$ is hydrogen)

Following the procedure of Example 2, but adding benzaldehyde (1.0 ml., 0.009 moles) at the start D-(+)-2-amino-2-phenylacetonitrile-hydrogen-L-(+)-tartrate is obtained, 9.72 g. (76% yield), $[\alpha]_D^{25}$ +40° ($c$ = 1, water).

EXAMPLE 20

Resolution of Racemic 2-Amino-2-phenylacetonitrile With 2-Butanone as the Catalyst (Formula III: R is phenyl; Formula IV: $R_1$ is methyl and $R_2$ is ethyl)

A solution of 2-amino-2-phenylacetonitrile (6.0 g., 0.045 mole) in toluene (20 ml.) is added to a solution of L-(+)-tartaric acid (6.6 g., 0.044 mole) in methanol (20 ml.) containing 2-butanone (1.0 ml., 0.011 mole). The mixture is seeded with D-(+)-2-amino-2-phenylacetonitrile-hydrogen-L-(+)-tartrate and stirred for 0.5 hour at 40° yielding a precipitate. The mixture is cooled to 20°. The precipitate is collected by filtration, washed with methanol and dried overnight at 40° under reduced pressure (40 mm) yielding D-(+)-2-amino-2-phenylacetonitrile-hydrogen-L-(+)-tartrate, 10.5 g. (84% yield), $[\alpha]_D^{25}$ +44° ($c$ = 1, water).

EXAMPLE 21

Resolution of Racemic 2-Amino-2-phenylacetonitrile With Cyclohexanone as the Catalyst (Formula III: R is phenyl; Formula IV: $R_1$ and $R_2$ taken together with the attached carbon atom is cyclohexanone)

A solution of 2-amino-2-phenylacetonitrile (26.4 g., 0.20 mole) in warm toluene (60 ml.) is added in portions to a slurry of L-(+)-tartaric acid (30.0 g., 0.20 moles) and cyclohexanone (10.3 ml., 0.10 mole) in methanol (50 ml.) at 40°. The mixture is stirred at 40° forming a precipitate. After 1 hour the mixture is cooled to 20°. The precipitate is collected by filtration, washed with toluene, then dried overnight at 40° under reduced pressure (40 mm) yielding D-(+)-2-amino-2-phenylacetonitrile-hydrogen-L-(+)-tartrate, 47.4 g. (84% yield, $[\alpha]_D^{25}$ +45° ($c$ = 1, water).

EXAMPLE 22

Resolution of Racemic 2-Amino-2-phenylacetonitrile With Cyclopentanone as the Catalyst (Formula III: R is phenyl; Formula IV: $R_1$ and $R_2$ taken together with the attached carbon atom is cyclopentanone)

The reaction of Example 21 is repeated at 50% scale and cyclopentanone (0.10 mole) is substituted in place of cyclohexanone. The product is D-(+)-2-amino-2-phenylacetonitrile-hydrogen-L-(+)-tartrate, 20.2 g. (72% yield), $[\alpha]_D^{25}$ +45° ($c$ = 1, water).

EXAMPLE 23

Resolution of Racemic 2-Amino-2-phenylacetonitrile With 2,2-Dimethoxypropane as the Catalyst (Formula III: R is phenyl; Formula IV: $R_1$ and $R_2$ are methyl, $R_1COR_2$ is in the methyl ketal form)

Following the procedure of Example 21, but substituting 2,2-dimethoxypropane (14 ml., 0.10 mole) for cyclohexanone, D-(+)-2-amino-2-phenylacetonitrile-hydrogen-L-(+)-tartrate is obtained, 43.5 g. (77% yield), $[\alpha]_D^{25}$ +45° ($c$ = 1, water).

EXAMPLE 24

Resolution of Racemic 2-Amino-2-phenylacetonitrile With α-ethylisovaleraldehyde (Formula III: R is phenyl; Formula IV: $R_1$ is 2-methyl-3-pentyl and $R_2$ is hydrogen)

Following the procedure of Example 21 but substituting α-ethylisovaleraldehyde (11.4 g., 0.1 mole) in place of cyclohexanone D-(+)-2-amino-2-phenylacetonitrile-hydrogen-L-(+)-tartrate is obtained, 40.5 g. (72% yield), $[\alpha]_D^{25}$ +44° ($c$ = 1, water).

EXAMPLE 25

Resolution of Racemic 2-Amino-2-(p-methoxyphenyl)acetonitrile With Acetone as the Catalyst (Formula III: R is p-methoxyphenyl; Formula IV: $R_1$ and $R_2$ are methyl)

Racemic 2-amino-2-(p-methoxypenyl)acetonitrile [D. F. Ewing, and D. G. Neilson, J. Chem. Soc, (C), 390 (1966)] (60.0 g., 0.370 mole) in 200 ml. of benzene is added to a solution of L-(+)-tartaric acid (63.0 g., 0.420 mole) and acetone (26.5 g., 0.420 mole) in methanol (200 ml.) at 40° under a nitrogen atmosphere. After 2 hours as 40° the reaction mixture is cooled, filtered and D-2-amino-2-(p-methoxyphenyl)acetonitrile-hydrogen-L-(+)-tartrate is obtained, 93.3 g. (81.2% yield), $[\alpha]_D^{25}$ +38° ($c = 1$, water).

EXAMPLE 26

Resolution of Racemic 2-amino-2-(p-methoxyphenyl)-acetonitrile with Benzaldehyde as the Catalyst (Formula III: R is p-methoxyphenyl; Formula IV: $R_1$ is phenyl, $R_2$ is hydrogen)

Following the procedure of Example 19, but substituting 2-amino-2-(p-methoxyphenyl)acetonitrile for 2-amino-2-phenylacetonitrile there is obtained D-2-amino-2-(p-methoxyphenyl)-acetonitrile-hydrogen-L-(+)-tartrate.

EXAMPLE 27

Resolution of Racemic 2-amino-2-(p-methoxyphenyl)acetonitrile with 2-Butanone as the Catalyst (Formula III: R is p-methoxyphenyl; Formula IV: $R_1$ is methyl and $R_2$ is ethyl)

Following the procedure of Example 20 for substituting 2-amino-2-(p-methoxyphenyl)acetonitrile for 2-amino-2-phenylacetonitrile, there is obtained D-2-amino-2-(p-methoxyphenyl)acetonitrile-hydrogen-L-(+)-tartrate.

EXAMPLE 28

Resolution of Racemic 2-amino-2-(p-hydroxyphenyl)-acetonitrile with Acetone as the Catalyst (Formula III: R is p-hydroxyphenyl; $R_1$ and $R_2$ are methyl)

Racemic 2-amino-2-(p-hydroxyphenyl) acetonitrile (U.S. Pat. No. 3,890,379, Example 1, m.p. 116°–117°; 1.48 gm, 0.010 moles) is added in small portions over 25 minutes to a solution of L-(+)-tartaric acid (1.50 g, 0.010 moles), acetone (3.1 ml. 0.043 moles), methanol (3.0 ml) and ethyl acetate (6.0 ml). The mixture is stirred under a nitrogen atmosphere at 40° for 1 hour, cooled to 20° and filtered to isolate the product. The product is washed with 5 ml of ethyl acetate:methanol (2:1) and dried at 40° under reduced pressure (40 mm). The product is D-2-amino-2-(p-hydroxyphenyl) acetonitrile-hydrogen-L-(+)-tartrate, 2.50 g. (84%), $[\alpha]_D^{25}$ +32° ($c = 3$, water).

A portion of this product (1.70 g, 0.0057 moles) is slurried for 1 hour at 40′ in a mixture of ethyl acetate (4 ml), methanol (2 ml) and acetone (2.1 ml). Work-up as described above gave D-2-amino-2-(p-hydroxyphenyl)-acetonitrile-hydrogen-L-(+)-tartrate, 1.44 g. (85%), $[\alpha]_D^{25}$ +42° ($c = 3$, water).

EXAMPLE 29

Resolution of Racemic 2-amino-2-(p-hydroxyphenyl)-acetonitrile with Benzaldehyde as the Catalyst (Formula III: R is p-hydroxyphenyl; Formula IV: $R_1$ is phenyl and $R_2$ is hydrogen)

Following the procedure of Example 19 but substituting 2-amino-2-(p-hydroxyphenyl)acetonitrile for 2-amino-2-phenylacetonitrile there is obtained D-2-amino-2-amino-2-(p-hydroxyphenyl)acetonitrile hydrogen-L-(+)-tartrate.

EXAMPLE 30

Resolution of Racemic 2-amino-2-(p-hydroxyphenyl)-acetonitrile with 2-Butanone as the Catalyst (Formula III: R is p-hydroxyphenyl; Formula IV: $R_1$ is methyl and $R_2$ is ethyl)

Following the procedure of Example 20 but substituting 2-amino-2-(p-hydroxyphenyl)acetonitrile (U.S. Pat. No. 3,890,379, Example 1) for 2-amino-2-phenylacetonitrile there is obtained D-2-amino-2-(p-hydroxyphenyl)acetonitrile-hydrogen-L-(+)-tartrate.

EXAMPLE 31

Production of Optically Pure D-(+)-2-Amino-2-phenylacetonitrile (Formula III: R is phenyl)

A solution of D-(+)-2-amino-2-phenylacetonitrile-hydrogen-L-(+)-tartrate (Example 3, 56.4 g. 0.20 mole) in distilled water (300 ml.) is stirred with methylene chloride (300 ml.) at 20° during slow addition of sodium carbonate (20.0 g., 0.19 mole) under a nitrogen atmosphere. The methylene chloride phase is then passed thru anhydrous sodium sulfate and the solvent removed at 20° under reduced pressure. The resultant oily product is crystallized from benzene-SSB at 10° to yield D-(+)-2-amino-2-phenylacetonitrile, 17.2 g. (69% yield), m.p. 55°–56°, $[\alpha]_D^{25}$ +52° ($c = 1$, chloroform).

EXAMPLE 32

Production of Optically Pure 2-Amino-2-phenylacetonitrile tartrate from Optically Pure 2-Amino-2-phenylacetonitrile of the Opposite Configuration (Formula III: R is phenyl; Formula IV: $R_1$ and $R_2$ are methyl)

A solution of optically pure D-(+)-2-amino-2-phenylacetonitrile (Example 31; 6.0 g., 0.045 mole) in 20 mol. of methanol-toluene (15:85 v/v) is added to a solution of D-(−)-tartaric acid (6.6 g., 0.044 mole) in methanol (20 ml.) containing acetone (3.36 ml., 0.046 mole). The mixture is stirred at 40°. After 10 minutes a precipitate begins to form. The mixture is stirred for 1 hour at 40° and then cooled to 20°. The precipitate is collected by filtration, washed with methanol, and dried overnight at 40° under reduced pressure (40 mm) to yield L-(−)-2-amino-2-phenylacetonitrile-hydrogen-D-(=)-tartrate, 10.5 g. (85% yield), $[\alpha]_D^{25}$ −46° ($c = 1$, water).

EXAMPLE 33

Production of Optically Pure 2-Amino-2-phenylacetonitrile tartrate from Optically Pure 2-Amino-2-phenylacetonitrile of the Opposite Configuration (Formula III: R is phenyl; Formula IV: $R_1$ and $R_2$ are methyl)

Following the general procedure of Example 32 but substituting L-(+)-tartaric acid for D-(−)-tartaric acid and L-(−)-2-amino-2-phenylacetonitrile for D-(+)-2-amino-2-phenylacetonitrile and making noncritical variations there is obtained D-2-amino-2-phenylacetonitrile-hydrogen-L-(+)-tartrate.

EXAMPLE 34

Production of Optically Pure 2-amino-2-phenylacetonitrile tartrate from a Non-Racemic Optically Impure 2-amino-2-phenyl-acetonitrile mixture (Formula III: R is phenyl; Formula IV: $R_1$ and $R_2$ are methyl)

Following the general procedure of Example 32, but starting with an optically impure mixture of 2-amino-2-phenylacetonitrile, $[\alpha]_D^{25}$ +26° ($c$ = 1, chloroform) which corresponds to a 25/75 mixture ($-/+$) and making noncritical variations there is obtained L-($-$)-2-amino-2-phenylacetonitrile-hydrogen-D-($-$)-tartrate, 10.35 g. (83%), $[\alpha]_D^{25}$ −45° ($c$ = 1, water).

EXAMPLE 35

Production of Optically Pure 2-amino-2-phenylacetonitrile tartrate from a Non-Racemic Optically Impure 2-amino-2-phenylacetonitrile mixture (Formula III: R is phenyl; Formula IV: $R_1$ and $R_2$ are methyl)

Following the general procedure of Example 34 but starting with an optically impure mixture of 2-amino-2-phenylacetonitrile which corresponds to a 75/25 mixture ($-/+$) and replacing D-[$-$]-tartaric acid with L-(+)-tartaric acid there is obtained D-(+)-2-amino-2-phenylacetonitrile-hydrogen-L-(+)-tartrate.

EXAMPLE 36

Hyrolysis of D-(+)-2-amino-2-phenylacetonitrile-hydrogen-L-(+)-tratrate to D-phenylglycine D-(+)-2-amino-2-phenylacetonitrile-hydrogen-L-(+)-tartrate (50 grams, 0.177 moles) in 195 ml. of 25 percent hydrochloric acid is heated for 2.3 hours at 95°. The mixture is cooled to 5° and filtered to obtain D-phenyl-glycine hydrochloride. D-phenylglycine hydrochloride is suspended in water and treated with sodiium hydroxide (25% solution) to a pH of 5.6. The mixture is cooled, filtered and the crystalline D-phenylglycine dried under reduced pressure (40 mm) at 40° overnight. The yield is 21.6 grams (81% yield) $[\alpha]_D^{25}$ −159° ($c$ = 4, 1N hydrochloric).

EXAMPLE 37

Hydrolysis of D-2-amino-2-(p-methoxyphenyl)-acetonitrile-L-(+)-tartrate to D-p-hydroxyphenylglycine D-2-amino-2-(p-methoxyphenyl)acetonitrile-hydrogen-L-(+)-tartrate (35.3 g., 0.113 mole) in a slurry with hydrobromic acid (80 ml. of 48%) and water (20 ml.) is heated at 95° for 2 hours. The mixture is then slowly heated to distill off some water (36 ml.). The mixture is cooled, Darco G-60 (2 g.) is added, mixed and filtered thru Celite. The filtrate is neutralized with 50% aqueous sodium hydroxide (37 ml.) to a pH of 6.8. The resultant precipitate is collected by filtration, washed once with methanol (10 ml.) and dried overnight at 40° under reduced pressure (40 mm). The product is D-p-hydroxyphenylglycine, 13.4 g. (71% yield), $[\alpha]_D^{25}$ −145°. Upon washing the product with water at 60° and drying, D-p-hydroxyphenylglycine is obtained in 63% overall yield, $[\alpha]_D^{25}$ −155°.

We claim:

1. A process for producing an optically pure 2-aminonitrile enantiomer of the formula:

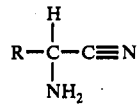

where R is alkyl of 1 thru 6 carbon atoms; cycloalkyl of 3 thru 6 carbon atoms; aromatic of 6 thru 10 carbon atoms, substituted with 0 thru 3 substituents, which may be the same or different and are selected from the group consisting of alkyl of 1 thru 6 carbon atoms, hydroxyl, alkoxy where the alkyl group contains 1 thru 6 carbon atoms, cyclic alkylenedioxy where the alkylene group contains 1 thru 3 carbon atoms, halogen, trifluoromethyl, and cyano; aralkyl of 7 or 8 carbon atoms substituted with 0 thru 3 substituents, which may be the same or different and are selected from the group consisting of alkyl of 1 thru 6 carbon atoms, hydroxyl, alkoxy where the alkyl group contains 1 thru 6 carbon atoms, or cyclic alkylenedioxy where the alkylene group contains 1 thru 3 carbon atoms; 2- or 3-furyl, 2- or 3-thienyl and 2- or 3-indolylmethyl in acid salt form in an amount greater than present in an optically impure 2-aminonitrile (III) mixture which comprises contacting the optically impure 2-aminonitrile (III) mixture with an optically active acid in the presence of a compound of the formula $R_1COR_2$ (IV), the methyl or ethyl actal, ketal, hemiacetal, or hemi-ketal thereof, where $R_1$ and $R_2$ may be the same or different with the proviso that both $R_1$ and $R_2$ cannot both be aromatic and where $R_1$ is alkyl of 1 thru 6 carbon atoms; cycloalkyl of 4 thru 6 carbon atoms; aromatic of 6 thru 10 carbon atoms, substituted with 0 thru 3 substituents selected from the group consisting of alkyl of 1 thru 6 carbon atoms, halogen, alkoxy where the alkyl group contains 1 thru 6 carbon atoms; or aralkyl of 7 or 8 carbon atoms; $R_2$ is hydrogen or $R_1$; and when $R_2$ is not hydrogen, $R_1$ and $R_2$ taken together with the attached carbon atom may form a cyclic ketone selected from the group consisting of cyclobutanone, cyclopentanone, cyclohexanone and cycloheptanone, and separating the diastereomeric acid salt of the optically pure 2-aminonitrile (III) enantiomer.

2. A process according to claim 1 where the 2-aminonitrile (III) is selected from the group consisting of 2-amino-2-phenylacetonitrile, 2-amino-2-(p-methoxyphenyl)acetonitrile, 2-amino-2-(p-hydroxyphenyl)acetonitrile, 2-amino-2-2-(3-chloro-4-hydroxyphenyl)acetonitrile, 2-amino-2-(2- or 3-furyl) acetonitrile or 2-amino-2-(2- or 3-thienyl)acetonitrile.

3. A process according to claim 2 where the optically active acid is selected from the group consisting of tartaric acid, diacetyl tartaric acid, dibenzoyl tartaric acid, di-p-toluyl tartaric acid, malic acid, camphoric acid, mandelic acid or menthoxyacetic acid.

4. A process according to claim 3 where the optically active acid is L-(+)-tartaric acid.

5. A process according to claim 4 wherein the 2-aminonitrile (III) is 2-amino-2-phenylacetonitrile.

6. A process according to claim 5 where the compound $R_1COR_2$ (IV) is acetone.

7. A process according to claim 4 where the 2-aminonitrile (III) is 2-amino-2-(p-methoxyphenyl)acetonitrile.

8. A process according to claim 7 where the compound $R_1COR_2$ (IV) is acetone.

9. A process according to claim 4 where the 2-aminonitrile is 2-amino-2-(p-hydroxyphenyl)acetonitrile.

10. A process according to claim 9 where the compound $R_1COR_2$ is acetone.

11. A process for resolving a racemic 2-aminonitrile mixture to greater than 50% yield of one enantiomer of the formula:

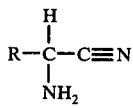   III in acid salt form which comprises contacting the racemic 2-aminonitrile (III) with an optically active acid in the presence of a compound of the formula $R_1COR_2$ (IV), the methyl or ethyl acetal, ketal, hemi-acetal, or hemi-ketal thereof, and separating the diastereomeric acid salt of the optically pure 2-aminonitrile (III) enantiomer, where R, $R_1COR_2$ (IV), $R_1$ and $R_2$ are defined in claim 1.

12. A process according to claim 11 where the 2-aminonitrile (III) is selected from the group consisting of 2-amino-2-phenylacetonitrile, 2-amino-2-(p-methoxyphenyl)-acetonitrile, 2-amino-2-(p-hydroxyphenyl)acetonitrile, 2-amino-2-(3-chloro-4-hydroxyphenyl)acetonitrile, 2-amino-2-(2- or 3-furyl)acetonitrile or 2-amino-2-(2-or 3-thienyl)-acetonitrile.

13. A process according to claim 12 where the optically active acid is selected from the group consisting of tartaric acid, diacetyl tartaric acid, dibenzoyl tartaric acid, di-p-toluyl tartaric acid, malic acid, camphoric acid, mandelic acid or menthoxyacetic acid.

14. A process according to claim 13 where the optically active acid is L-(+)-tartaric acid.

15. A process according to claim 14 where the 2-aminonitrile (III) is 2-amino-2-phenylacetonitrile.

16. A process according to claim 15 where the compound $R_1COR_2$ (IV) is acetone.

17. A process according to claim 15 wherein the compound $R_1COR_2$ (IV) is benzaldehyde.

18. A process according to claim 15 where the compound $R_1COR_2$ (IV) is 2-butanone.

19. A process according to claim 15 where the compound $R_1COR_2$ (IV) is cyclohexanone.

20. A process according to claim 15 where thhe compound $R_1COR_2$ (IV) is cyclopentanone.

21. A process according to claim 15 where the compound $R_1COR_2$ (IV) is 2,2-dimethoxypropane.

22. A process according to claim 15 where the compound $R_1COR_2$ (IV) is α-ethylisovaleraldehyde.

23. A process according to claim 14 where the 2-aminonitrile (III) is 2-amino-2-(p-methoxyphenyl)acetonitrile.

24. A process according to claim 23 where the compound $R_1COR_2$ (IV) is acetone.

25. A process according to claim 23 where the compound $R_1COR_2$ (IV) is benzaldehyde.

26. A process according to claim 23 where the compound $R_1COR_2$ (IV) is 2-butanone.

27. A process according to claim 14 where the 2-aminonitrile (III) is 2-amino-2-(p-hydroxyphenyl)acetonitrile.

28. A process according to claim 27 where the compound $R_1COR_2$ (IV) is acetone.

29. A process according to claim 27 where the compound $R_1COR_2$ (IV) is benzaldehyde.

30. A process according to claim 27 where the compound $R_1COR_2$ (IV) is 2-butanone.

31. A process for producing an optically pure 2-aminonitrile enantiomer of the formula:

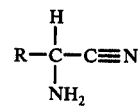   III in acid salt form which comprises contacting the optically pure 2-aminonitrile enantiomer of the opposite configuration with an optically active acid in the presence of a compound of the formula $R_1COR_2$ (IV), a methyl or ethyl acetal, ketal, hemi-acetal, or hemi-ketal thereof, and separating the diasteromeric acid salt of the optically pure 2-aminoninitrile (III) enantiomer, where R, $R_1COR_2$ (IV), $R_1$ and $R_2$ are defined in claim 1.

32. A process according to claim 31 where the 2-aminonitrile (III) is selected from the group consisting of 2-amino-2-phenylacetonitrile, 2-amino-2-(p-methoxyphenyl)-acetonitrile, 2-amino-2-(p-hydroxyphenyl)acetonitrile, 2-amino-2-(3-chloro-4-hydroxyphenyl)acetonitrile, 2-amino-2-(2- or 3-furyl)acetonitrile or 2-amino-2-(2- or 3-thienyl)-acetnoitrile.

33. A process according to claim 32 where the optically active acid is selected from the group consisting of tartaric acid, diacetyl tartaric acid, dibenzoyl tartaric acid, di-p-toluyl tartaric acid, malic acid, camphoric acid, mandelic acid or menthoxyacetic acid.

34. A process according to claim 33 where the optically active acid is L-(+)-tartaric acid.

35. A process according to claim 34 where the 2-aminonitrile (III) is 2-amino-2-phenylacetonitrile.

36. A process according to claim 35 where the compound $R_1COR_2$ (IV) is acetone.

37. A process for resolving racemic 2-amino-2-phenylacetonitrile to greater than 50% yield of D-(+)-2-amino-2-phenylacetonitrile-hydrogen-L-(+)-tartrate which comprises contacting racemic 2-amino-2-phenylacetonitrile with optically active L-(+)-tartaric acid and acetone.

* * * * *